United States Patent [19]
Cronin

[11] Patent Number: 4,706,658
[45] Date of Patent: Nov. 17, 1987

[54] GLOVED SPLINT

[76] Inventor: Penny S. Cronin, 421 W. Lajolla, Tempe, Ariz. 85282

[21] Appl. No.: 866,608

[22] PCT Filed: Sep. 10, 1985

[86] PCT No.: PCT/US85/01723
§ 371 Date: May 14, 1986
§ 102(e) Date: May 14, 1986

[87] PCT Pub. No.: WO86/01707
PCT Pub. Date: Mar. 27, 1986

[30] Foreign Application Priority Data

Sep. 14, 1984 [DE] Fed. Rep. of Germany ....... 3433795

[51] Int. Cl.⁴ .................. A61F 5/04; A61F 5/10
[52] U.S. Cl. ............................ 128/77; 128/87 R; 128/87 A; 128/DIG. 20
[58] Field of Search ............ 128/26, 77, 87 A, 87 R, 128/DIG. 20; 2/159, 161 R, 163, 164, 16

[56] References Cited

U.S. PATENT DOCUMENTS

4,000,585  1/1977  Denaro ................ 135/115 X
4,173,218  11/1979  Cronin .................. 128/77

FOREIGN PATENT DOCUMENTS

0270341  9/1913  Fed. Rep. of Germany ........ 128/87

Primary Examiner—Robert A. Hafer
Assistant Examiner—Kathleen J. D'Arrigo
Attorney, Agent, or Firm—Cahill, Sutton & Thomas

[57] ABSTRACT

A gloved splint is adapted for use in conjunction with physical therapy necessitated by injury or disease and to preclude grotesque distortion of the fingers due to rheumatoid arthritis induced muscle contractions. Hinged finger splints, with or without a hinged thumb splint, extending from a palm splint, permit flexing of specific joints in normal manner while precluding sideways flexing at any of the joints; moreover, inflexible or particularly molded finger and/or thumb splints may be incorporated to assist particular therapeutic treatment. A glovelike envelope, fillable with a fluid, incapsulates the hand, fingers and thumb and provides a shock absorbent buffer to minimize transmission of painful blows and jolts to the hand; a further envelope attendant a wrist portion of the glove serves as a reservoir for delivering fluid to and receiving fluid from the glovelike envelope. Insulation, vents and fluid transfer capability may be included to minimize pain, to increase comfort or assist therapy through application or withdrawal of heat.

23 Claims, 8 Drawing Figures

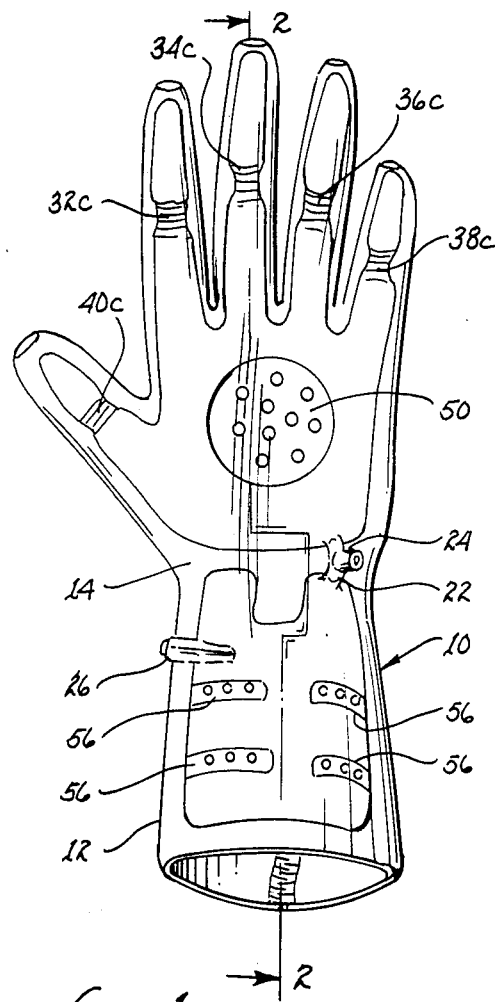
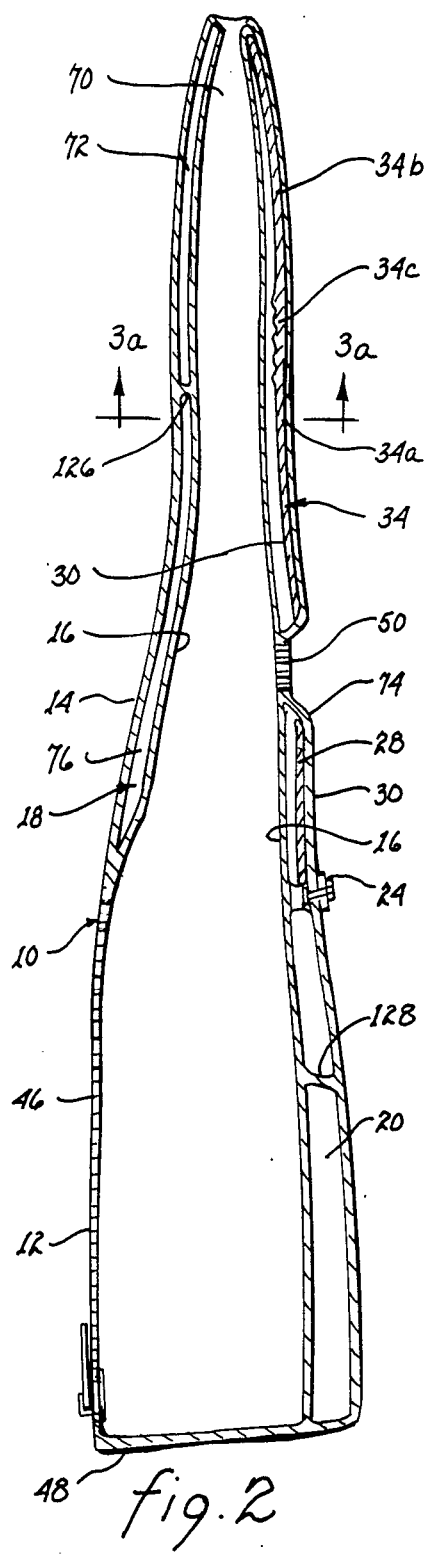
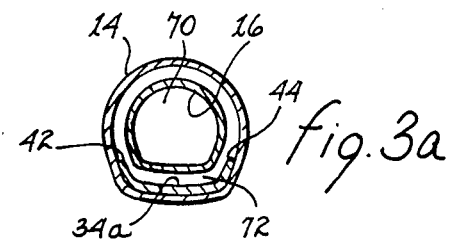
fig. 1
fig. 2
fig. 3a
fig. 3b

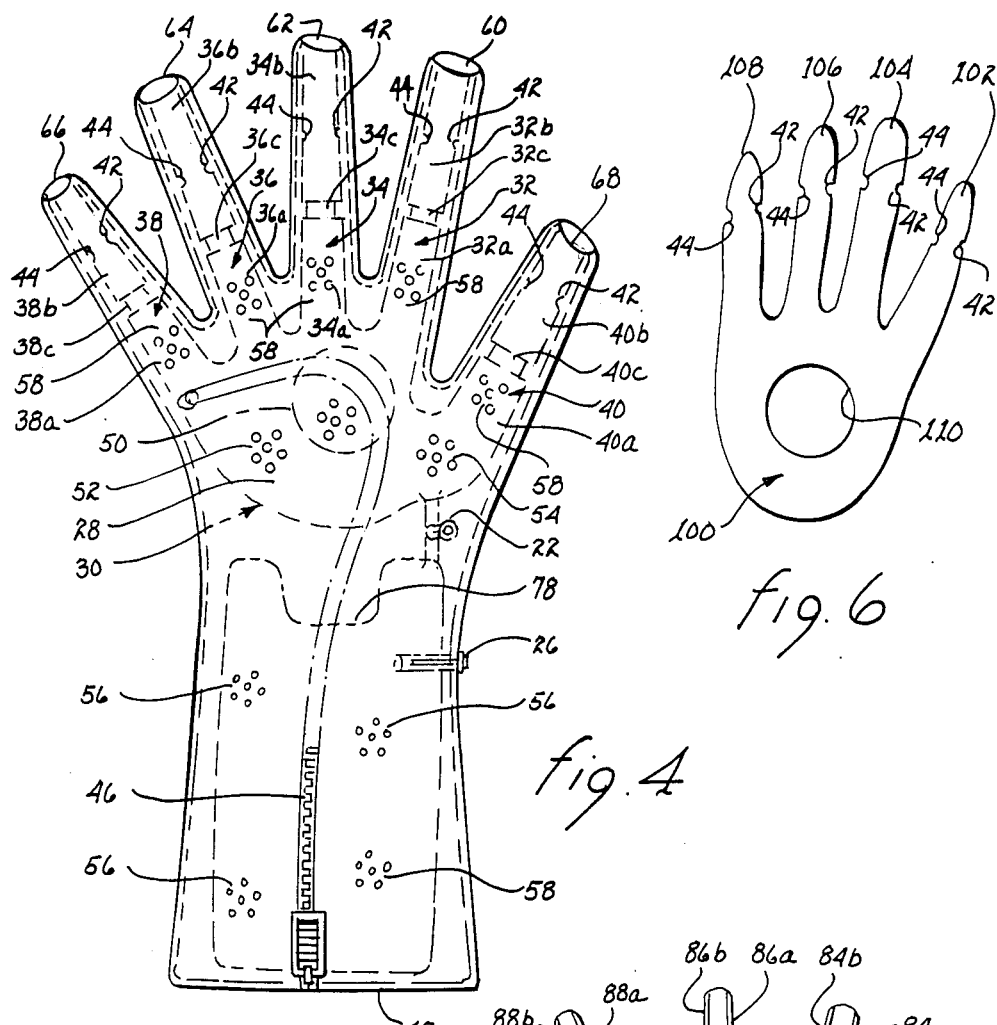
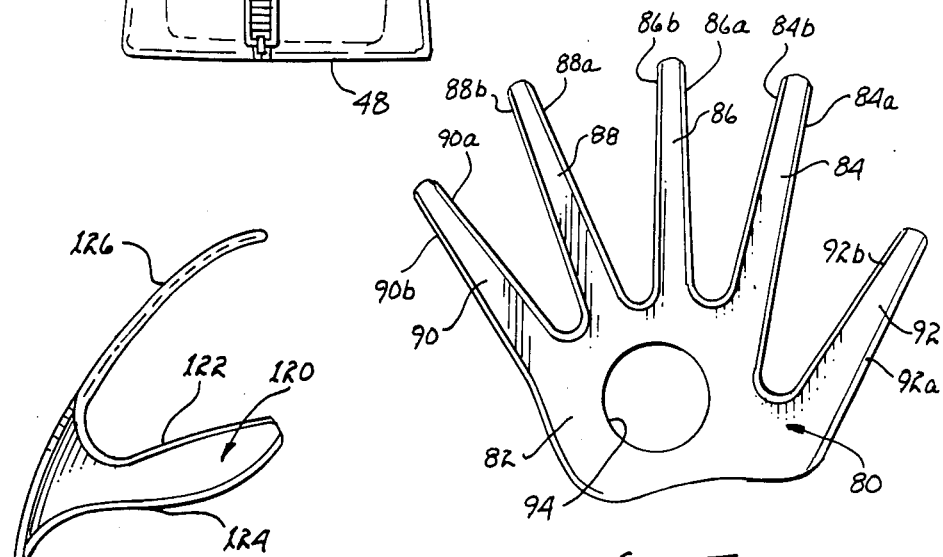

GLOVED SPLINT

The present invention is directed to an improvement of the gloved splint invented by the present inventor and described in U.S. Pat. No. 4,173,218 entitled "GLOVED SPLINT FOR AN ARTHRITIC HAND."

The present invention relates to splints, and more particularly, to splints for use with rheumatoid arthritis stricken hands and for assisting in therapeutic treatment of hands.

The word "arthritis" literally means "inflammation of a joint." Rheumatoid arthritis is the most serious, the most painful and most potentially crippling of the nearly one hundred rheumatic diseases. Deformed hands, twisted legs, stooped shoulders and stiff elbows are often the most miserable signs of the disease. It can strike suddenly and progress rapidly to an acute and seriously damaging stage.

Rheumatoid arthritis usually invades more than one joint. The joint stiffens, swells and becomes tender, eventually making full motion difficult and painful. The aching, soreness and stiffness are typically at their worst when the victim first gets up in the morning.

Rheumatoid inflammation does progressive damage inside the joint. If it is not checked by proper treatment, the following may happen. The space where two bones meet is enclosed in a capsule containing fluid. The capsule has an inner skin called the synovil membrane. Inflammation begins here, swells the membrane and spreads to other parts of the joint system. Outgrowths of inflamed tissue invade the cartilage surrounding the bone ends, eventually eating it away. Finally, scar tissue can form between the bone and sometimes change to bone so that the joint becomes fused, permanently rigid and immovable.

While a joint is undergoing this destruction, muscle contractions can cause grotesque distortions. This is most apparent when the disease attacks the hands. The fingers can become skewed or drawn back and sideways, so that the hand becomes deformed. It is important to understand that this can happen but it can be prevented in most cases with proper treatment before it does happen. The key to success in combatting the effects of rheumatoid arthritis is a treatment program of many parts carried out faithfully over a period of time. Such a program may include medication, exercise, rest, surgery, heat, posture correction, splints and rehabilitation. The purposes of the treatment program are to relieve pain, reduce inflammation and prevent damage to the joints, prevent deformaties and keep the joints movable and functioning properly.

Presently, splints now in use to help prevent grotesque distortions of the hand, are made of plaster of paris or of a high or low temperature thermo plastic. These are generally intended for short periods of use because of the nature of the construction. Moreover, they are inflexible and do not allow any movement of the affected body parts. Accordingly, they cannot be used repetitively by the afflicted person nor do they provide the benefits of exercising the affected joints. Generally, after surgery, specially constructed splints are sometimes applied to the affected joint. These splints are special purpose splints predicated upon the particular needs of the patient; since they are custom made, they are expensive.

Applying or withdrawing heat from an affected joint is often beneficial in alleviating the pain and discomfort attendant the joint.

Therapy of a damaged hand resulting from injury or disease may include splinting of the hand in a predetermined position to render it immobile for defined periods. Other treatment may suggest limited predetermined movement of all or parts of the hand. During the treatment process, progressive positioning of the hand or parts thereof from one position to another may be extremely beneficial commensurate with growth or recuperation of muscle, skin and bone tissues. Such progressive repositioning may be coupled with predeterminable limited flexing of parts of the hand. The application or withdrawal of heat in conjunction with or separate from the above described treatment schedules may be of great recuperative value under certain circumstances.

A large number of U.S. patents have issued which describe various gloved heating devices for use with one's hands, including: U.S Pat. Nos. 542,177, 1,970,081, 3,292,628, 3,465,120, 3,569,666, 3,621,191, 3,632,966, 3,649,966 and 4,021,640. Other U.S. patents relating to heating elements for various part of the body include Pat. Nos. 885,112, 2,071,706 and 2,706,988. Various splints directly attachable to a hand are described in U.S. Pat. Nos. 270,341, 1,220,476, 1,817,212 and 3,581,740. Inflatable bags for repositioning the fingers of a hand are described in U.S. Pat. Nos. 735,700 and 3,937,215.

The various devices illustrated in the above-identified identified patents can, because of their bulk or thickness, insulate the affected part against the sharpness of any jolts or blows. However, this benefit is essentially incidental to the prime purpose of the devices. A very common problem with arthritic hands is that of calcification of the knuckles which, by limiting flexing of the joints, results in atrophy of the finger muscles. Such atrophy, in turn, in combination with functions not fully understood, generally results in muscle contractions which skew the fingers at the knuckles. The skewing, in a regenerative manner, exacerbates the problem. Similarly, splinted hands which are precluded from regular movement or exercise tend to result in weakness or atrophy of finger muscles and flexibility of the joints intermediate the very many bones within the hand. Such atrophy must be attended subsequent to removal of the splint and further prolongs the treatment necessary unless onset of atrophy can be prevented or at least restrained.

In the preferred embodiment of the present invention, a splint extends across the palm and includes extensions for supporting the fingers and perhaps the thumb. The extensions include tabs or sidewalls for restraining lateral movement of the fingers and thumb from a predeterminable relationship to one another and the palm of the hand; thereby, skewing of the finger and thumb digits is precluded. The extensions may include hinges located at predetermined finger and thumb joints to permit flexing at such joints. For particular therapeutic treatment, the splint may be configured to retain the palm, fingers and thumb in a predetermined cupped or curled position, with or without flexing of any of the associated joints. An envelope encasing the whole hand may be filled with a fluid to serve as a buffering medium; in addition, the fluid can serve as a heat retaining element to provide a source of warmth or it may be chilled to retain the hand in a cool environment. The fluid can also provide a pressurizing effect to help relieve inflammation and/or edema of the hand and wrist. The cuff of the glove extends a sufficient distance upward the forearm to allow flexing to an extent compatible with the ongoing treatment and such cuff may be used as a reservoir for filling and withdrawing fluid from within the envelope about the hand and wrist. Ventilation holes may be provided in juxtaposed relationship to the forearm, the back of the hand, the palm and individual fingers and thumb to provide for an air flow in conjunction with the open fingertips of the glove. A curved zipper extending from the forearm portion to the portion adjacent the back of the hand provides a large opening through which the hand may be inserted and removed with facility and minimal pain to a user.

It is therefore a primary object of the present invention to provide a removable splint for an arthritis stricken hand.

Another object of the present invention is to provide a splint which will restrain movements of the fingers, thumb to predetermined excursions.

Yet another object of the present invention is to provide a splint usable during nighttime to prevent uncontrollable muscular contractions tending to skew a user's fingers and thumb.

Still another object of the present invention is to provide a ventilation system for a splint to withdraw heat generated by inflamed joints of an arthritis stricken hand.

A further object of the present invention is to provide a reservoir for encasing with a fluid medium a hand damaged by arthritis or injury.

A yet further object of the present invention is to provide a gloved splint for heating or cooling a damaged hand by controlling a flow of fluid thereabout.

A still further object of the present invention is to provide a universally usable gloved splint wherein the splint may be uniquely configured to promote therapeutic treatment of a damgaged hand.

These and other objects of the present invention will become apparent to those skilled in the art as a description thereof proceeds.

The present invention may be described with greater specificity and clarity with reference to the following drawings, in which:

FIG. 1 is a palm perspective view of the present invention;

FIG. 2 is a cross-sectional view taken along lines 2—2, as shown in FIG. 1;

FIG. 3a is a cross-sectional view taken along lines 3a—3a, as shown in FIG. 2 and FIG. 3b illustrates a variant thereof;

FIG. 4 is a top view of a variant of the present invention;

FIG. 5 illustrates a variant of the splint usable in conjunction with the present invention;

FIG. 6 illustrates a further variant of the splints; and

FIG. 7 is representative of the capability for using a uniquely molded splint as part of the present invention.

Referring jointly to FIGS. 1 and 2, there is shown a gloved splint or hand protector having a glove 10 configured as a fingered glove for receiving the fingers, thumb, palm, wrist and lower forearm of a user. Wrist portion 12 extends for a distance along the forearm and preferably maintains the wrist joint in a neutral position or at a slight extension. This latter configuration restrains or prevents undesired cocking of the wrist perhaps resulting from uncontrollable muscle contraction. Such contraction, as discusssd above, may occur conjointly with deterioration of the wrist joint due to rheumatoid arthritis or due to the spasmodic muscular contractions resulting from other injury or disease. To further constrain wrist movement without necessarily rendering the wrist completely rigid, straps, elastic or reinforcing members may be incorporated with wrist portion 12 to provide the requisite restraint.

Glove 10 includes an outer covering 14 and an inner lining 16 which, in combination, define an envelope having two primary components, a hand/wrist related envelope 18 and a forearm related envelope 20. The two envelopes may be in fluid communication with one another through a conduit 22 having a valve 24 cooperatively associated therewith for limiting flow through the conduit from one envelope to the other. This valve may be configured to also be capable of filling and evacuating the respective envelopes. Alternatively, access to the envelopes may be through petcock or valve 26 in fluid communication with envelopes 18 and 20. It is to be understood that the locations of valves 24 and 26, if used, may be varied, as dictated by therapeutic and practical reasons.

A sheet of stiff, but not necessarily rigid, material is juxtaposed with the inner surface of outer covering 14 in proximity to the palm and defines palm portion 28 of splint 30, as particularly illustrated in FIGS. 2 and 4. In certain embodiments, a pouch, as represented by numeral 31 in FIG. 3b, may be formed as part of glove 10 to removably receive and retain the related finger splint; it is to be understood that similar pouch means can be incorporated as part of outer covering 14 to removably receive and retain palm portion 28 of splint 30. In other embodiments, the splint may be removably retained in place by a combination of friction and pressure or by an adhesive. Splint 30 includes finger splints 32, 34, 36 and 38 and thumb splint 40. These finger and thumb splints may include first and second segments 32a, 32b, 34a, 34b, 36a, 36b, 38a, 38b and 40a, 40b hingedly interconnected by hinge means 32c, 34c, 36c, 38c and 40c respectively. Each of the finger and thumb splints provides support for the respective finger and thumb while accommodating flexing at the joint coincident with the respective hinge means. To preclude disassociation of the fingers and thumb from the respective splints, lateral movement constraint means such as opposed tabs 42, 44 may be incorporated in one or both of the segments of each finger and thumb splint.

As splint 30 is maintained in position with respect to the palm by the at least somewhat form fitting glove or other means as discussed above, the splint is capable of little, if any, movement relative to the palm of the user. Moreover, finger splints 32-38 and thumb splint 40, being an integral part of or fixedly attached to palm portion 28, cannot move relative to the palm portion. By restraining one or another digit of each finger and thumb to its respective splint through the above enumerated tabs or like lateral constraints, the knuckle of each finger is maintained essentially immobile. Thereby, the fingers and thumb are precluded from skewing laterally at the knuckles due to muscle contractions attendant rheumatoid arthritis. The use of hinge means 32c, 34c, 36c, 38c and 40c, positionally corresponding to a joint, permits pivotal movement of the second segment with respect to the first segment and independent movement of the fingertips and thumbtip. Such flexing movement permits the user to grip various objects and perform other manipulative functions not possible were the fingers rendered totally immobile.

It is generally difficult and normally very painful to insert an arthritic hand or hand damaged due to injury or other disease into a conventional glove. To alleviate the discomfort of donning and removing the gloved splint described herein, a zipper 46 extends from wrist opening 48 and along a curved path across the back of the glove; other configurations are also contemplated. Thereby, access to the interior of the glove is available through a relatively large opening and insertion or withdrawal of one's fingers, thumb, palm and wrist is relatively easy and relatively painless. On closing of zipper 46, the body of the gloved splint and wrist portion are brought into snug engagement with the hand. It is to be understood that closure means other than a zipper may be incorporated.

Arthritically inflamed joints often have a tendency to generate heat. When such heat is confined, it may exacerbate the pain. To preclude heat build-up due to the arthritic joint itself or because of high ambient temperatures, a ventilator 50 may be disposed in the palm portion of glove 10. Similar ventilators 52, 54 may be disposed in the glove adjacent the back of the hand. Additional ventilators 56 may be developed in wrist portion 12. Yet further ventilators 58 may be formed in the finger and thumb portions of the glove. It is to be understood that splint 30 also incorporates apertures juxtaposed with any ventilators of the glove. The terminal ends 60, 62, 64, 66 and 68 of the finger portions and thumb portions of glove 10 are purposely truncated as part of the ventilation system of the glove to provide an opening through which the air may flow.

As particularly illustrated in FIG. 3a, there is shown a cross-section of a representative finger or thumb of glove 10. Outer covering 14 supports first segment 34a of palm splint 30 from which segment tabs 42, 44 may extend into cavity 72. Outer covering 14, in combination with inner lining 16 defines a cylindrical-like cavity 72 (a part of envelope 18) extending about the middle finger. As depicted in part FIG. 3b, a pouch 31 may be secured external to outer covering 14 to removably or permanently receive a part of splint 30.

As illustrated in FIG. 1, hinge means 32c, 34c, 36c, 38c and 40c may be formed as a flexible, but integral, component of splint 30 rather than being a separate hinge mechanism interconnecting the first and second segments of the respective finger splints and thumb splint. Moreover, the finger and thumbtips may be necked down, as illustrated in FIGS. 1 and 2, to provide a cover for essentially the full length of the respective fingers and thumb; alternatively, terminal ends 60, 62, 64, 66 and 68 may terminate at a point short of or commensurate with the respective finger and thumbtips, as suggested by FIG. 4.

Referring jointly to FIGS. 1-4, the fluid containment system attendant glove 10 will be described in further detail. Envelope 20 developed in wrist portion 12, serves primarily the function of a reservoir for injecting fluid into or receiving fluid from envelope 18. The underside of the forearm proximate the wrist includes a number of pressure senstive nerves and major blood vessels for the hand. Any pressure there against over a period of time may cause pain and discomfort. To insure against creation of such presure point, envelope 20 includes an indentation 78 generally commensurate with this area to prevent pressure there against by any fluid within the envelope. Envelope 18, represented by cavity 72 attendant each of the fingers and thumb and by cavity 74 attendant the palm and further cavity 76 juxtaposed with the back of the hand, provides the primary jolt buffer to the hand encased within glove 10. The shape and depth of portions of envelope 18 may be varied or variously configured to best provide the particular benefits sought by a user.

For certain therapeutic or medical reasons, the amount of fluid within envelope 18 may be increased or decreased to apply greater or lesser pressure to the hand. Such increase or decrease may be easily accommodated by opening valve 24 to permit fluid flow from envelope 20 into envelope 18 or vice versa. Therapeutic benefits of glove 10 include the possibility of relieving inflammation in arthrtiic hands or edema from flaccid hands by controlling swelling through pressurizing the fluid within envelope 18.

As discussed above, glove 10 may be used for multiple purposes. For certain purposes, immobility of the fingers and thumb may be of paramount importance. In such event, splint 80 shown in FIG. 5 may be substituted for splint 30 in glove 10. Splint 80 includes a palm portion 82 having rigid finger splints 84, 86, 88, 90 and thumb splint 92 extending therefrom. These finger and thumb splints may be straight or curved, depending upon the therapy to be administered. To insure retention of the fingers and thumb with the respective finger and thumb splints, each finger splint and thumb splint may be formed as a C-channel in cross-section; that is, the respective finger and thumb splints include sidewalls 84a, 84b, 86a, 86b, 88a, 88b, 90a, 90b and 92a, 92b to provide restraint against lateral movement of the respective fingers and thumb. Splint 80 may include an aperture 94 or plurality of apertures to coincide with corresponding ventilators of glove 10.

Under certain circumstances, the use of a thumb splint may not be necessary or desired. In such event, splint 100 illustrated in FIG. 6 may be employed. Herein, finger splints 102, 104, 106 and 108 are depicted as rigid splints. When necessary, splint 100 may include hinged finger splints of the type depicted in FIG. 4. Tabs 42, 44 or channels of the type depicted in FIG. 5 may be employed to retain the fingers adjacent the respective splints. An aperture or a plurality of apertures 110 are incorporated to coincide with corresponding ventilators in glove 10.

For particular hand rehabilitation treatments or programs, it may be beneficial to employ a specially configured splint to locate each finger and thumb in a particular orientation with respect to the palm. The possibility of using such splint in conjunction with glove 10 is represented by splint 120 in FIG. 7. It is presently contemplated that such a splint can be readily and accurately developed by presently known thermo plastic construction techniques. For representative purposes, splint 120 includes readily incorporatable sidewalls 122, 124 and 126 attendant the finger and thumb splints to retain the respective fingers and thumb coincident therewith. Although not shown, it is contemplated that hinge means may be incorporated if flexing of one or more fingers or thumb is preferable.

Baffle means, functionally represented by cross member 126 in cavity 72 (envelope 18) and cross member 128 in envelope 20 (FIG. 2), may be employed to constrain rapid fluid shift due to jolts or localized pressure points. The baffle means could be just a certain arrangement of the ventilators that would inhibit rapid movements of the fluid within envelopes 18 and 20 or the baffle means could be actual fluid constraint chambers that would be interconnected by various fluid pathways or channels. Also, some perhaps porous material could act to impede the rapid flow of fluid within envelopes 18 and 20 brought on by certain hand positions or movements. Similarly, the channels within envelopes 18 and 20 could simply be existing fluid pathways around and/or to the baffle means and ventilators. Or, the channels could be artificially constructed conduits to feed and interconnect the baffle means within envelopes 18 and 20.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A hand protector for supporting and protecting selected ones of the fingers and thumb of a disease stricken or injured hand, said hand protector comprising in combination:
   (a) a palm splint positionable in juxtaposed relationship to the palm of the hand;
   (b) selected ones of finger splints and a thumb splint extending from said palm splint for supporting the respective fingers and thumb in a predetermined relationship to the palm of the hand;
   (c) glove means for maintaining said palm splint and said selected finger splints and thumb splint in juxtaposed relationship with the corresponding parts of the hand, said glove means including;
      i. a first envelope for holding fluid in juxtaposed relationship with at least a portion of the parts of the hand supported by said palm splint, and the selected ones of said finger splints and said thumb splint;
      ii. a wrist portion for engaging the wrist and a part of the forearm of a user;
      iii. a second envelope developed within said wrist portion for holding fluid;
      iv. means for interconnecting said first and second envelopes to accommodate flow of fluid therebetween;
      v. means for exposing and for maintaining exposed the tips of the respective supported ones of the fingers and thumb; and
      vi. means for discouraging application of pressure by any fluid within said second envelope of said glove means against the under side of the wrist.

2. A hand protector as set forth in claim 1 including valve means in fluid communication with said second envelope for filling and evacuating said second envelope.

3. A hand protector as set forth in claim 2 wherein said interconnecting means comprises a valve.

4. A hand protector as set forth in claim 1 including closure means for securing a hand within said glove means, said closure means being oriented to permit opening of said glove means along and across the back of the hand.

5. A hand protector as set forth in claim 4 wherein said closure means defines a curved line.

6. A hand protector as set forth in claim 1 including ventilators disposed in said glove means for ventilating an encased hand.

7. A hand protector as set forth in claim 6 including further ventilators disposed in said wrist portion.

8. A hand protector as set forth in claim 7 wherein said further ventilators comprise baffles to impede fluid flow within said second envelope.

9. A hand protector as set forth in claim 6 wherein said palm splint includes apertures positionally correspondent with said ventilators.

10. A hand protector as set forth in claim 1 including means for baffling the flow of fluid within said first envelope.

11. A hand protector as set forth in claim 1 including means for baffling the flow of fluid within said second envelope.

12. A hand protector as set forth in claim 11 including means for baffling the flow of fluid within said first envelope.

13. A hand protector as set forth in claim 1 including means for channeling the flow of fluid within said first envelope.

14. A hand protector as set forth in claim 1 wherein each of the selected ones of said finger splints is rigid to support the respective finger in a curved position equivalent in curvature to the curved configuration of the respective finger when the hand is in the at rest position.

15. A hand protector as set forth in claim 1 wherein each of the selected ones of said finger splints includes hinge means for accommodating flexing of the respective finger proximate at least one of the finger joints.

16. A hand protector as set forth in claim 1 wherein each of the selected ones of said finger splints includes means for restraining lateral movement of the respective one of the fingers relative to said finger splint.

17. A hand protector as set forth in claim 16 wherein the selected ones of said finger splints and said thumb splint includes said thumb splint and wherein said thumb splint includes means for restraining lateral movement of the thumb relative to said thumb splint.

18. A hand protector as set forth in claim 1 wherein said palm splint, selected ones of said finger splints and said thumb splint are curved to support a hand in a predetermined configuration.

19. A hand protector as set forth in claim 1 wherein said glove means includes pouch means for retaining in place said palm splint.

20. A hand protector as set forth in claim 19 wherein said pouch means extends along the finger portions of said glove means for receiving the respective ones of said finger splints.

21. A hand protector as set forth in claim 1 wherein said discouraging means includes an area in said wrist portion adjacent the underside of a user's wrist which is devoid of said second envelope.

22. A hand protector as set forth in claim 1 including means for selectively locating at least one of said finger splints and said thumb splint within said glove means.

23. A hand protector as set forth in claim 22 wherein said locating means includes a pouch.

* * * * *